(12) United States Patent
Grinberg et al.

(10) Patent No.: US 6,770,095 B2
(45) Date of Patent: Aug. 3, 2004

(54) INTERVERTEBRAL DISC

(75) Inventors: Alexander Grinberg, Newton, MA (US); Michael D. Sorrenti, Middleboro, MA (US); Andrew Dooris, Fall River, MA (US); Melissa Grace, E. Falmouth, MA (US); Missoum Moumene, West Newton, MA (US)

(73) Assignee: Depuy Acroned, Inc., Raynham, MA (US)

( * ) Notice: Subject to any disclaimer, the term of this patent is extended or adjusted under 35 U.S.C. 154(b) by 162 days.

(21) Appl. No.: 10/174,457

(22) Filed: Jun. 18, 2002

(65) Prior Publication Data

US 2003/0233146 A1 Dec. 18, 2003

(51) Int. Cl.[7] .................................................. A61F 2/44
(52) U.S. Cl. ................................................. 623/17.14
(58) Field of Search .......................... 623/17.11, 17.12, 623/17.13, 17.14, 17.15, 17.16; 606/61

(56) References Cited

U.S. PATENT DOCUMENTS

| | | | |
|---|---|---|---|
| 5,370,697 A | 12/1994 | Baumgartner | |
| 5,507,816 A | 4/1996 | Bullivant | |
| 5,676,701 A | 10/1997 | Yuan et al. | |
| 5,683,465 A | * 11/1997 | Shinn et al. | 623/17.14 |
| 5,881,802 A | 3/1999 | Green | |
| 5,895,428 A | * 4/1999 | Berry | 623/17.15 |
| 6,039,763 A | 3/2000 | Shelokov | |
| 6,063,121 A | 5/2000 | Xavier | |
| 6,113,637 A | 9/2000 | Gill et al. | |
| 6,368,350 B1 | 4/2002 | Erickson et al. | |
| 6,527,804 B1 | * 3/2003 | Gauchet et al. | 623/17.12 |
| 6,645,249 B2 | * 11/2003 | Ralph et al. | 623/17.13 |
| 6,669,730 B2 | * 12/2003 | Ralph et al. | 623/17.13 |
| 6,679,915 B1 | * 1/2004 | Cauthen | 623/17.11 |
| 2003/0135278 A1 | * 7/2003 | Eckman | 623/17.14 |
| 2003/0216810 A1 | 11/2003 | Ralph et al. | |

FOREIGN PATENT DOCUMENTS

EP   0 282 161 A   9/1988

* cited by examiner

Primary Examiner—Pedro Philogene
(74) Attorney, Agent, or Firm—Thomas M. DiMauro

(57) ABSTRACT

This invention relates to an intervertebral motion disc having an articulation interface and a locking interface.

40 Claims, 12 Drawing Sheets

INTERVERTEBRAL DISC

BACKGROUND OF THE INVENTION

The leading cause of lower back pain arises from rupture or degeneration of lumbar intervertebral discs. Pain in the lower extremities is caused by the compression of spinal nerve roots by a bulging disc, while lower back pain is caused by collapse of the disc and by the adverse effects of bearing weight through a damaged, unstable vertebral joint. One conventional method of managing these problems is to remove the problematic disc and replace it with a prosthetic disc that allows for the natural motion between the adjacent vertebrae ("a motion disc").

U.S. Pat. No. 5,676,701 ("Yuan") discloses a motion disc including a first component whose inner surface comprises a concave inner portion having a 360° circumference and a convex peripheral portion, and an opposing second component whose inner surface comprises a conforming convex inner portion and a convex peripheral portion. The convex/concave contours of the opposing inner portions forms a ball-and-socket design that allows unrestricted pivotal motion of the device, while the opposing convex peripheral contours allow flexion/extension bending motion in the range of about 20–30°.

However, neither component of the Yuan device limits the extent to which the articulation surface may become vertical disengaged. Restraint of the pivotal motion in this device is provided by the contours of the opposing peripheral surfaces. Moreover, the articulating surfaces of Yuan are relatively small in area, limited to the middle third of the device.

U.S. Pat. No. 5,507,816 ("Bullivant") discloses a three-piece motion disc comprising an upper piece having a flat lower surface, a middle spacer having a flat upper surface and a convex lower surface, and a lower piece having a concave upper surface. The articulating convex and concave surfaces form an articulating interface that allows pivotal motion, while the flat surfaces form a translation interface that allows translational motion. Bullivant further teaches that the natural tension of the vertebrae ensures that the vertebrae are biased together to trap the spacer in place, and that the 90° extension of the convex and concave surfaces virtually eliminates any chance of the spacer escaping from between the upper and lower pieces under normal pivotal movement of the vertebrae.

Since Bullivant relies upon natural tension to keep the components in place, none of the components is designed to limit the vertical disengagement of the articulation surfaces. Restraint of the pivotal motion appears to be provided by the peripheral portions of the inner surfaces of the upper and lower components (i.e., downwardly flat facing surface 28 and upwardly flat facing surface 30). Moreover, Bullivant does not teach a two piece design. The articulating surfaces of Bullivant are relatively small in area, limited to the middle half of the device.

U.S. Pat. No. 6,113,637 ("Gill") discloses a motion disc having a ball and socket articulation, wherein the trough of the socket has a flat portion. The ball and socket geometry provides pivotal motion while the flat portion of the trough allows the ball to slide, thereby providing some translation motion.

Gill relies upon independent rigid fixation of each component to its respective vertebral endplate as the means for limiting vertical disengagement of its articulation surfaces. Restraint on pivotal motion of the device is provided by rim 57 extending laterally from the perimeter of the socket, and by the rigid fixation of the upper and lower components to their respective vertebrae. Gill is a non-conforming design. The size of the articulating surfaces of Gill is relatively small when compared to the overall size of the motion disc.

U.S. Pat. No. 6,039,763 ("Shelokov") discloses a motion disc that articulates in a manner resembling the human knee. The disc comprises an articulating concave/convex interface which is bimodal in nature along its lateral plane. In one embodiment, the convex surface features a gradually changing radius of curvature along its anterior-posterior ("A-P") plane so that A-P flexion provides for A-P translation. In one embodiment, the concave surface includes A-P channels adapted to permit lateral—lateral translation. Lastly, the pair of concave shaped surfaces can be separated by a raised surface to provide a gentle braking of the lateral—lateral translation.

The Shelokov device is non-conforming in both the lateral and A-P planes. There appears to be no means for limiting vertical disengagement of its articulation surfaces. Restraint on pivotal motion of the device is provided by the raised surface between the concave surfaces.

Therefore, there is a need for a motion disc that limits the vertical disengagement of the articulating surfaces.

SUMMARY OF THE INVENTION

The present inventors have found that providing a prosthetic motion disc with a locking means advantageously limits the extent of normal disengagement of an articulation interface of the disc during normal use.

The locking means may include any structure located on or in connection with a first prosthetic vertebral endplate that limits the normal disengagement of the articulating surfaces by physically interacting with a structure located on or in connection with the second prosthetic vertebral endplate.

In one embodiment, there is provided a two-piece design comprising first and second prosthetic vertebral endplates, and a locking means holding the two prosthetic vertebral endplates together. In one preferred embodiment, a portion of the locking means extends from one of the articulating surfaces. In another preferred embodiment, the articulation interface is formed in part by an articulation surface formed upon a projection portion of the locking means. Preferably, the articulation interface allows for pivotal motion in any direction, and axial rotation.

Therefore, in accordance with the present invention, there is provided a motion disc comprising:
 a) a first prosthetic vertebral endplate having
  i) an outer surface adapted to mate with a first vertebral body,
  ii) an inner surface comprising a first articulation surface, and
 b) a second prosthetic vertebral endplate having
  i) an outer surface adapted to mate with a second vertebral body,
  ii) an inner surface comprising a second articulation surface, and
 c) locking means for limiting the extent of disengagement of the first articulation surface from the second articulation surface.

Preferably, the first and second articulation surfaces are adapted to form an articulating interface.

The present inventors have also found that in preferred embodiments, the device can include a pair of locking surfaces adapted to limit the normal disengagement of the articulating surfaces.

Accordingly, also in accordance with the present invention, there is provided a motion disc comprising:
a) a first prosthetic vertebral endplate having
   i) an outer surface adapted to mate with a first vertebral body,
   ii) an inner surface comprising a first articulation surface, and
   iii) a locking surface, and
b) a second prosthetic vertebral endplate having
   i) an outer surface adapted to mate with a second vertebral body,
   ii) an inner surface comprising a second articulation surface, and
   iii) a locking surface,
wherein the first and second articulation surfaces are adapted to form an articulating interface, and
   wherein the first and second locking surfaces are adapted to form a locking interface.

Since, in preferred embodiments, each prosthetic vertebral endplate of the prosthetic device has both an articulating surface and a locking surface, in accordance with the present invention, there is provided a prosthetic vertebral endplate for use in a motion disc, the prosthetic vertebral endplate comprising:
   i) an outer surface adapted to mate with a vertebral body, and
   ii) an inner surface comprising an articulation surface, and
   iii) a locking surface.

In many embodiments, the locking surface is located on the inner surface of the prosthetic vertebral endplate. In many embodiments, the locking surface and the articulation surface face substantially opposite directions.

DETAILED DESCRIPTION OF THE INVENTION

For the purposes of the present invention, an "articulation interface" includes any interface adapted to provide at least one type of natural motion between vertebral bodies, including pivotal motion, translational motion and rotational motion. An articulation interface can be conforming or non-conforming.

For the purposes of the present invention, a surface within a recess extending from the inner surface of a prosthetic vertebral endplate is considered to be part of the inner surface of the prosthetic vertebral endplate.

For the purposes of the present invention, "prosthetic vertebral endplate" broadly describes a component designed to substantially fit within an interverterbal space and mate with an opposing surface of one of the adjacent vertebral bodies. The "prosthetic vertebral endplate" includes all geometric configurations, including but not limited to substantially thin and substantially blocky configurations. Types of mating include, but are not limited to, penetrating the adjacent vertebral body, simply contacting the adjacent vertebral body, and providing fixation through a third component such as a fastener (such as a screw) that is received within or connected to the prosthetic vertebral endplate. Such fixation may occur upon a non-opposing surface of the adjacent vertebral body (such as the anterior wall of the vertebral body). The adjacent vertebral body may be prepared or unprepared so that the contacting surface thereof may include the cortical end endplate portion of the vertebral body or the internal cancellous portion of the vertebral body.

Figure 1:
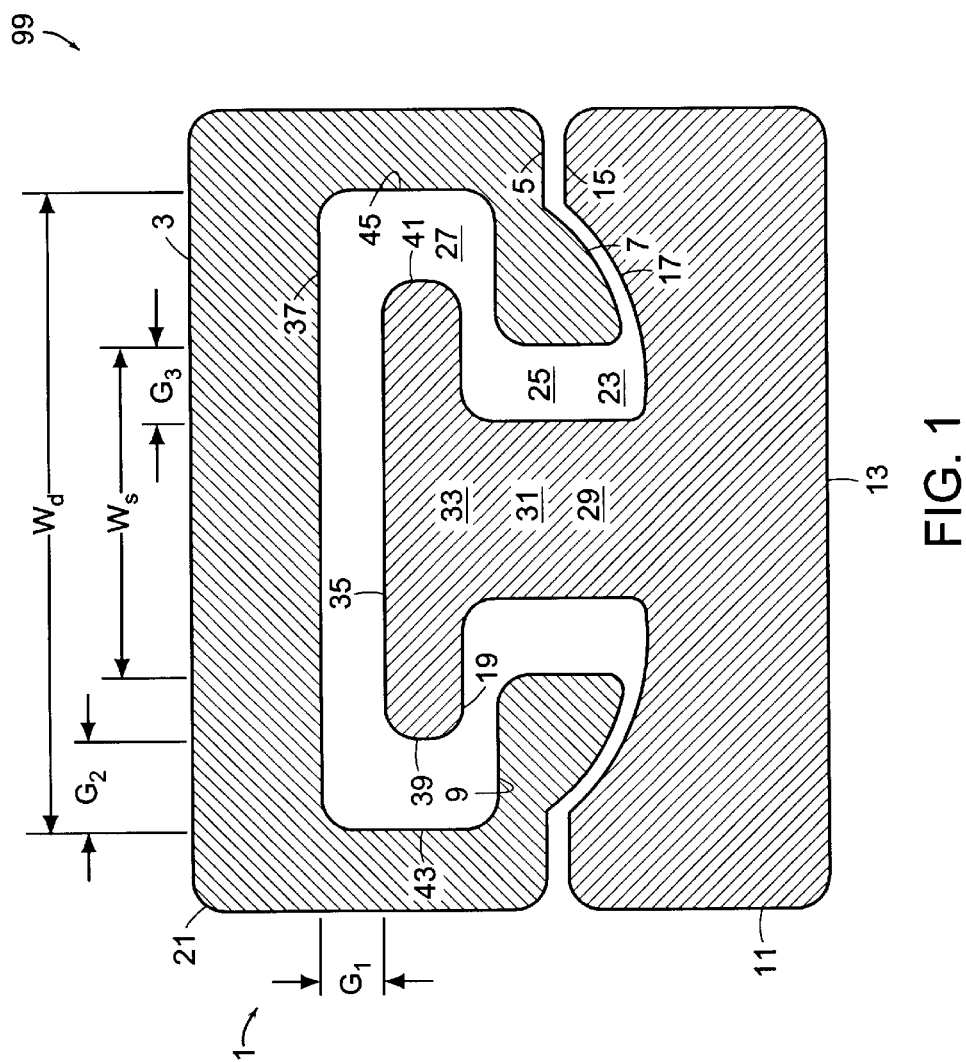
FIG. 1 discloses a cross section of a first embodiment of the present invention.

Now referring to FIG. 1, there is provided a motion disc 99 comprising:
a) a first prosthetic vertebral endplate 1 having:
   i) an outer surface 3 adapted to mate with a first vertebral body,
   ii) an inner surface 5 comprising a first articulation surface 7,
   iii) a body portion 21 located between the inner and outer surfaces, and
   iv) a recess 23 extending from the inner surface into the body portion and forming a first locking surface 9, and
b) a second prosthetic vertebral endplate 11 having:
   i) an outer surface 13 adapted to mate with a second vertebral body,
   ii) an inner surface 15 comprising a second articulation surface 17 and a projection 29 extending from the second articulation surface and comprising a shank 31 and an enlarged end portion 33 forming a second locking surface 19,
wherein the first and second articulation surfaces are adapted to form a conforming articulating interface,
wherein the first and second locking surfaces are adapted to form a locking interface, and wherein the recess has a shallow portion 25 having a width Ws and a deep portion 27 having a width Wd, wherein the width of the deep portion is greater than the width of the shallow portion.

In normal use, articulation surfaces 7 and 17 will articulate with one another in one or more types of motion. However, there may be extreme activity that acts to separate the articulation surfaces 7 and 17, thereby producing normal disengagement of the articulation interface. When the disengagement proceeds to the extent that locking surface 19 of the projection comes into contact with the locking surface 9 of the recess, these surfaces 9 and 19 advantageously limit the extent of such normal disengagement of the articulation interface.

The device of FIG. 1 further contains a means for restraining the articulating motion of the device. In this case, the extent of pivotal motion may be determined by the depth of any number of gaps formed between the projection and the recess, including: a) a first gap $G_1$ between the end surface 35 of the projection and the deep surface 37 formed by the recess, b) a second gap $G_2$ formed between the lateral ends 39,41 of the enlarged head and the lateral walls 43,45 of the deep portion of the recess, and c) a third gap $G_3$ formed between the diameter of the shank 31 and the diameter of the shallow portion 25 of the recess. When normal activity causes an extreme articulation such that the surfaces that determine a gap come in contact with each other, such contact acts to restrain the articulating motion of the device.

In preferred embodiments, the gaps are provided such that the articulating interface is limited to between 10 and 15 degrees (and preferably about 13 degrees) of A-P motion, and between 5 and 10 degrees (and preferably about 6 degrees) of lateral motion, As it is believed that each prosthetic vertebral endplate shown in FIG. 1 by itself possesses advantageous novelty over those conventional prosthetic vertebral endplates, in accordance with the present invention, there is provided a prosthetic vertebral endplate for use in a vertebral motion disc comprising:

a) an outer surface adapted to mate with a first vertebra,
b) an inner surface having a projection extending therefrom, wherein at least a portion of the inner surface is adapted to form an articulating surface, and wherein the projection has an inner portion having a width and a outer portion having a width, wherein the width of the outer portion is greater than the width of the inner portion.

Also in accordance with the present invention, there is provided a prosthetic vertebral endplate for use in a vertebral motion disc comprising:

a) an outer surface adapted to mate with a second vertebra,
b) an inner surface,
c) a body portion between the inner and outer surfaces, and
d) a recess extending from the inner surface into the body portion, wherein at least a portion of the inner surface is adapted to form an articulating surface, and,
wherein the recess has a shallow portion having a width and a deep portion having a width, wherein the width of the deep portion is greater than the width of the shallow portion.

The first prosthetic vertebral endplate 1 of FIG. 1 may be either the upper or lower prosthetic vertebral endplate. Preferably, however, the first prosthetic vertebral endplate is the lower prosthetic vertebral endplate.

Figure 2:
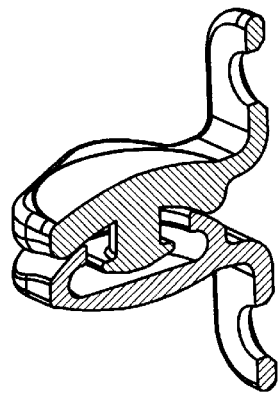
FIG. 2 discloses a cross sectioned embodiment of the present invention.

FIGS. 2–5 disclose a more detailed device of the present invention having a locking means substantially similar to that shown in FIG. 1. Now referring to FIG. 2, which shows a cross-section of the assembled prosthetic vertebral endplates, the locking means comprises the mushroom-shaped projection located on the upper prosthetic vertebral endplate, and the recess located on the lower prosthetic vertebral endplate. The articulation interface of the device of FIG. 2 is provided by a ball and socket design comprising the first and second articulating surfaces. Accordingly, in this embodiment, the projection does not form a portion of the articulating surface.

Also, in this embodiment shown in FIG. 2, articulating surfaces 7 and 17 extend essentially to the periphery of the inner surface of their respective prosthetic vertebral endplates. Because of the essentially full extension of these surfaces to the periphery, the periphery of the inner surface does not act as a limitation on the range of motion of the device. In contrast, the periphery of the inner surface of the Yuan device acts as a limitation on the range of pivotal motion.

In addition, the essentially full extension of these surfaces to the periphery increases the surface area of the articulation interface, thereby reducing the stress upon the articulation surfaces and likely reducing the wear of the articulation surfaces. Preferably, at least one (and more preferably both) of the articulation surfaces has a surface area which is at least 80% (and more preferably, at least 90%) of the periphery of a footprint of its respective prosthetic vertebral endplate.

Figure 3:
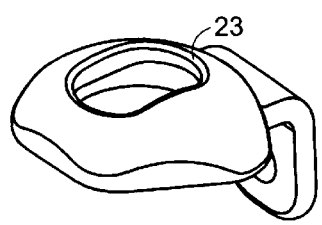
FIG. 3 discloses a perspective view of the lower prosthetic vertebral endplate of the embodiment of FIG. 2.
Figure 4:
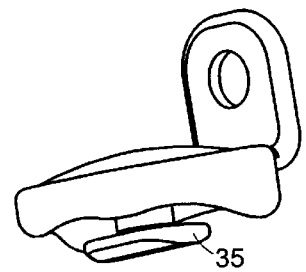
FIG. 4 discloses a perspective view of the upper prosthetic vertebral endplate of the embodiment of FIG. 2.

Now referring to FIG. 3, which shows the lower prosthetic vertebral endplate of FIG. 2 alone, the shallow portion 23 of the recess forms a rectangular shape whose longer dimension is oriented in the anterior-posterior direction. Now referring to FIG. 4, which shows the upper prosthetic vertebral endplate of FIG. 2 alone, the enlarged end portion of the projection forms a rectangular end surface 35 whose longer dimension is oriented in the lateral direction. The cross-sectional area of the shallow portion 23 of the recess is slightly larger than that of the rectangular end surface 35 so that the rectangular end surface 35 may pass therethrough. In use, the two rectangular shapes are aligned, the enlarged end portion of the projection is passed through the shallow portion of the recess and enters the deep portion of the recess. Then one of the prosthetic vertebral endplates is rotated about 90 degrees relative to the other. Since the longer dimension of the rectangular end surface 35 is greater than the shorter dimension of shallow portion 23, the enlarged end portion of the projection can not easily re-enter the shallow portion of the recess, but rather becomes locked in the deep portion of the recess.

Figure 5:
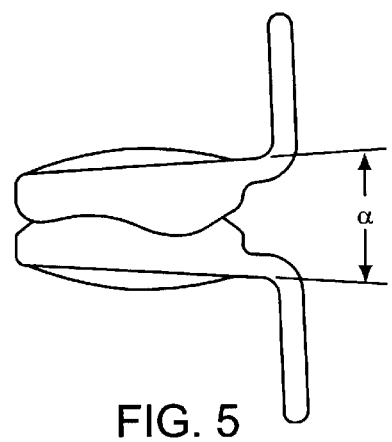
FIG. 5 discloses a perspective view of an assembled embodiment of FIG. 2.

Now referring to FIG. 5, a perspective view of the assembled disc is shown. Preferably, the contours of the outside surfaces of the respective prosthetic vertebral endplates are such that, when the shank of the projection is disposed substantially parallel to the shallow portion of the recess, the outside surfaces are not parallel but rather form an angle α in the A-P direction. Preferably, the outside surfaces are adapted to provide a lordotic angle in the A-P direction. A lordotic angle is desirable because the natural anatomical disposition of the disc space in the lumbar region of the spine is lordotic (i.e., produces a forward lean). Preferably, the outside surfaces are adapted to provide a lordotic angle of between 5 and 10 degrees, more preferably between 6 and 8 degrees, most preferably about 7 degrees.

In the particular embodiment shown in FIGS. 2–5, the projection extends from the concave articulating surface of the upper prosthetic vertebral endplate, while the recess extends from the convex articulating surface of the lower prosthetic vertebral endplate. In other embodiments, the locations of the articulating surfaces may be reversed. For example, the projection may extend from a convex portion of an upper prosthetic vertebral endplate and the recess may extend from a concave portion of a lower prosthetic vertebral endplate. Similarly, the locations of the projection and recess may be reversed. For example, the projection may extend from a convex articulating surface of the lower prosthetic vertebral endplate and the recess may extend from a concave articulating surface of the upper prosthetic vertebral endplate. Lastly, the projection may extend from a concave articulating surface of the lower prosthetic vertebral endplate and the recess may extend from a convex articulating surface of the upper prosthetic vertebral endplate Also in accordance with the present invention, and now referring to FIG. 6, there is provided a vertebral motion disc 199 comprising:

a) a first prosthetic vertebral endplate 101 having an outer surface 103 adapted to mate with a first vertebra, and inner surface 105 having a projection 129 extending therefrom, the projection having an outer end portion 130 forming an outer articulating surface 131, b) a second prosthetic vertebral endplate 111 having a outer surface 113 adapted to mate with a second vertebra, an inner surface 115, a body portion 121 between the inner and outer surfaces, and a recess 123 extending from the inner surface into the body portion and forming an inner articulating surface 133, wherein the outer articulating surface of the projection and the inner articulating surface of the recess form a conforming articulating interface,
wherein the recess 123 has a shallow portion 125 having a width Ws and a deep portion 127 having a width Wd, wherein the width of the deep portion is greater than the width of the shallow portion.

Figure 6:
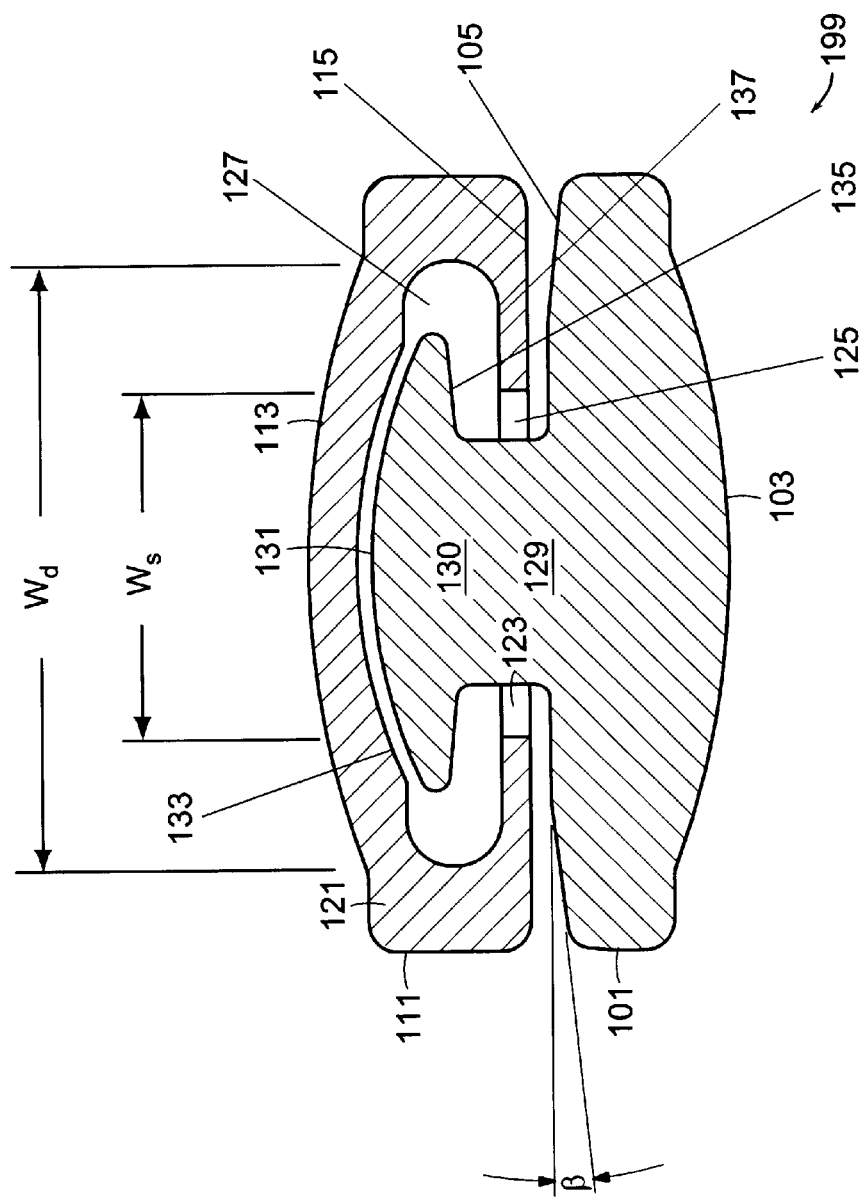
FIG. 6 discloses a cross section of a second embodiment of the present invention.
Figure 7:
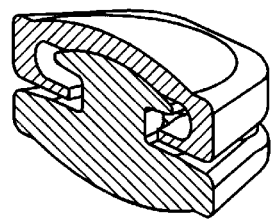
FIG. 7 discloses a cross sectioned embodiment of the present invention.
Figure 8:
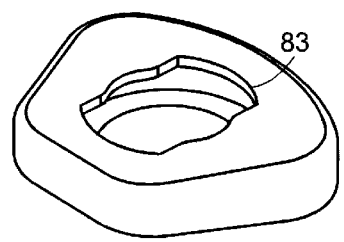
FIG. 8 discloses a perspective view of the upper prosthetic vertebral endplate of the embodiment of FIG. 7.
Figure 9:
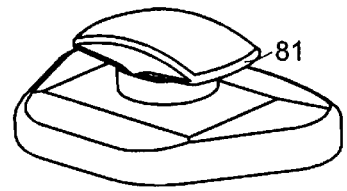
FIG. 9 discloses a perspective view of the lower prosthetic vertebral endplate of the embodiment of FIG. 7.

The device shown in FIG. 6 principally differs from that of FIG. 1 in that whereas the inner surfaces of the device of FIG. 1 form an articulation interface and the projection of FIG. 1 comprises merely a locking surface, the inner surfaces 115,105 of the device of FIG. 6 do not form an articulation interface (but are merely shaped to limit the desired range of motion of the device), and the projection 129 of FIG. 6 comprises not only a locking surface but also an articulation surface.

Referring again to FIG. 6, the limitation of the normal disengagement of the prosthetic vertebral endplates is provided by locking surface 135 of the projection when it comes into contact with the locking surface 137 of the recess.

In some embodiment as in FIG. 6, the range of motion of the device may be limited by the peripheral portion of the inner surfaces. In this case, the contours of the peripheral portions of the inner surfaces of the respective prosthetic vertebral endplates are such that, when the shank of the projection is disposed substantially parallel to the shallow portion of the recess, the peripheral portions of the inner surfaces are not parallel but rather form an angle β. In preferred embodiments, the contours of the peripheral portions of the inner surfaces of the respective prosthetic vertebral endplates are such that the angle β is limited to between 10 and 15 degrees (and preferably about 13 degrees) of A-P direction, and preferably between 5 and 10 degrees (and preferably about 6 degrees) of lateral direction.

As it is believed that each prosthetic vertebral endplate shown in FIG. 6 by itself possesses advantageous novelty over those conventional prosthetic vertebral endplates, in accordance with the present invention, there is provided a prosthetic vertebral endplate for use in a vertebral motion disc comprising:

a) an outer surface adapted to mate with a first vertebra,
b) an inner surface having a projection extending therefrom, the projection forming an outer face, wherein at least a portion of the outer surface of the projection is adapted to form an articulating surface, and wherein the projection has an inner portion having a width and a outer portion having a width, wherein the width of the outer portion is greater than the width of the inner portion.

Also in accordance with the present invention, there is provided a prosthetic vertebral endplate for use in a vertebral motion disc comprising:

a) an outer surface adapted to mate with a second vertebra, b) an inner surface, c) a body portion between the inner and outer surfaces, and d) a recess extending from the inner surface into the body portion, the recess forming an inner surface, wherein at least a portion of the inner surface of the recess is adapted to form an articulating surface, and wherein the recess has a shallow portion having a width and a deep portion having a width, wherein the width of the deep portion is greater than the width of the shallow portion.

In the particular embodiment shown in FIG. 6, the projection extends from the lower prosthetic vertebral endplate, while the recess extends into the upper prosthetic vertebral endplate. In other embodiments, the locations of the projection and recess may be reversed. For example, the projection may extend from the lower prosthetic vertebral endplate and the recess may extend from the upper prosthetic vertebral endplate. When the projection extends from the lower prosthetic vertebral endplate and the recess extends from the upper prosthetic vertebral endplate, the articulation surface is formed at a lower position (i.e. within the lower prosthetic vertebral endplate), and so is more stable.

Figure 10:
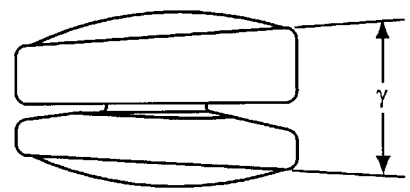
FIG. 10 discloses a perspective view of an assembled embodiment of FIG. 7.

FIGS. 7–10 disclose a more detailed device of the present invention having a locking means substantially similar to that shown in FIG. 6. Now referring to FIG. 7, which shows a cross-section of the assembled prosthetic vertebral endplates, the locking means comprises the mushroom-shaped projection located on the lower prosthetic vertebral endplate, and a recess located on the upper prosthetic vertebral endplate. Now referring to FIG. 8, the shallow portion 83 of the recess defines a rectangular shape whose longer dimension is oriented in the anterior posterior direction. Now referring to FIG. 9, the enlarged end portion of the projection forms a rectangular end surface 81 whose longer dimension is oriented in the lateral direction. The size of the shallow portion of the recess is slightly larger than that of the enlarged end portion of the projection so that the enlarged end portion may pass therethrough. In use, the two rectangular shapes are aligned, the enlarged end portion projection is passed through the shallow portion of the recess, and then one prosthetic vertebral endplate is rotated about 90 degrees so that the enlarged end portion of the projection becomes locked in the deep portion of the recess. The assembled disc is shown in FIG. 10.

Now referring to FIG. 10, a perspective view of the assembled disc is shown. Preferably, the contours of the outside surfaces of the respective prosthetic vertebral endplates are such that, when the shank of the projection is disposed substantially parallel to the shallow portion of the recess, the outside surfaces are not parallel but rather form an angle γ in the A-P direction. Preferably, the outside surfaces are adapted to provide a lordotic angle in the A-P direction. Preferably, the outside surfaces are adapted to provide a lordotic angle of between 5 and 10 degrees, more preferably between 6 and 8 degrees, most preferably about 7 degrees.

The present invention may also be provided in various embodiments in which the locking means is provided at different locations on the device, as shown below.

Figure 11:
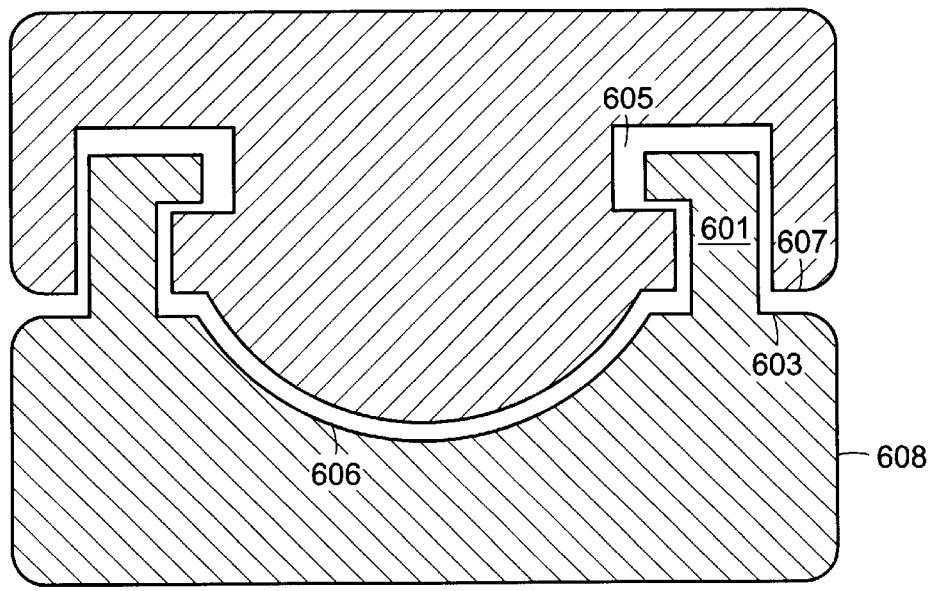
FIGS. 11–19 disclose cross sections of various embodiments of the present invention.

Now referring to FIG. 11, there is provided another embodiment of the present invention wherein the locking means comprises a projection 601 extending from the peripheral portion 603 of an inner surface of a first prosthetic vertebral endplate and fitting into a recess 605 extending from a peripheral portion 607 of an inner surface of a second prosthetic vertebral endplate.

Figure 12:
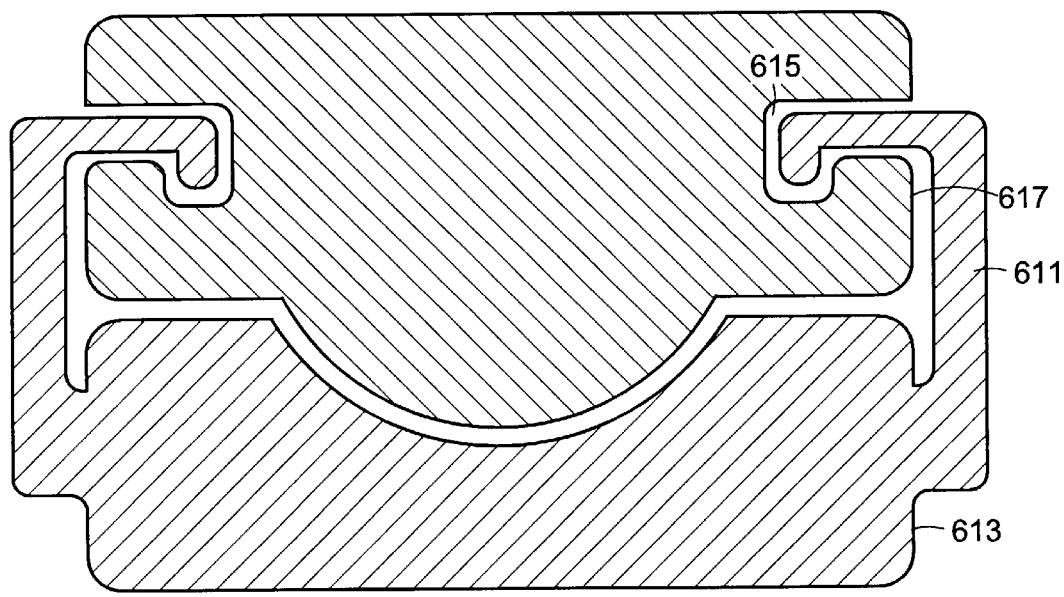

Now referring to FIG. 12, wherein the locking means comprises a projection 611 extending from a sidewall 613 of a first prosthetic vertebral endplate and fitting into a recess 615 extending from a sidewall 617 of a second prosthetic vertebral endplate.

Figure 13:
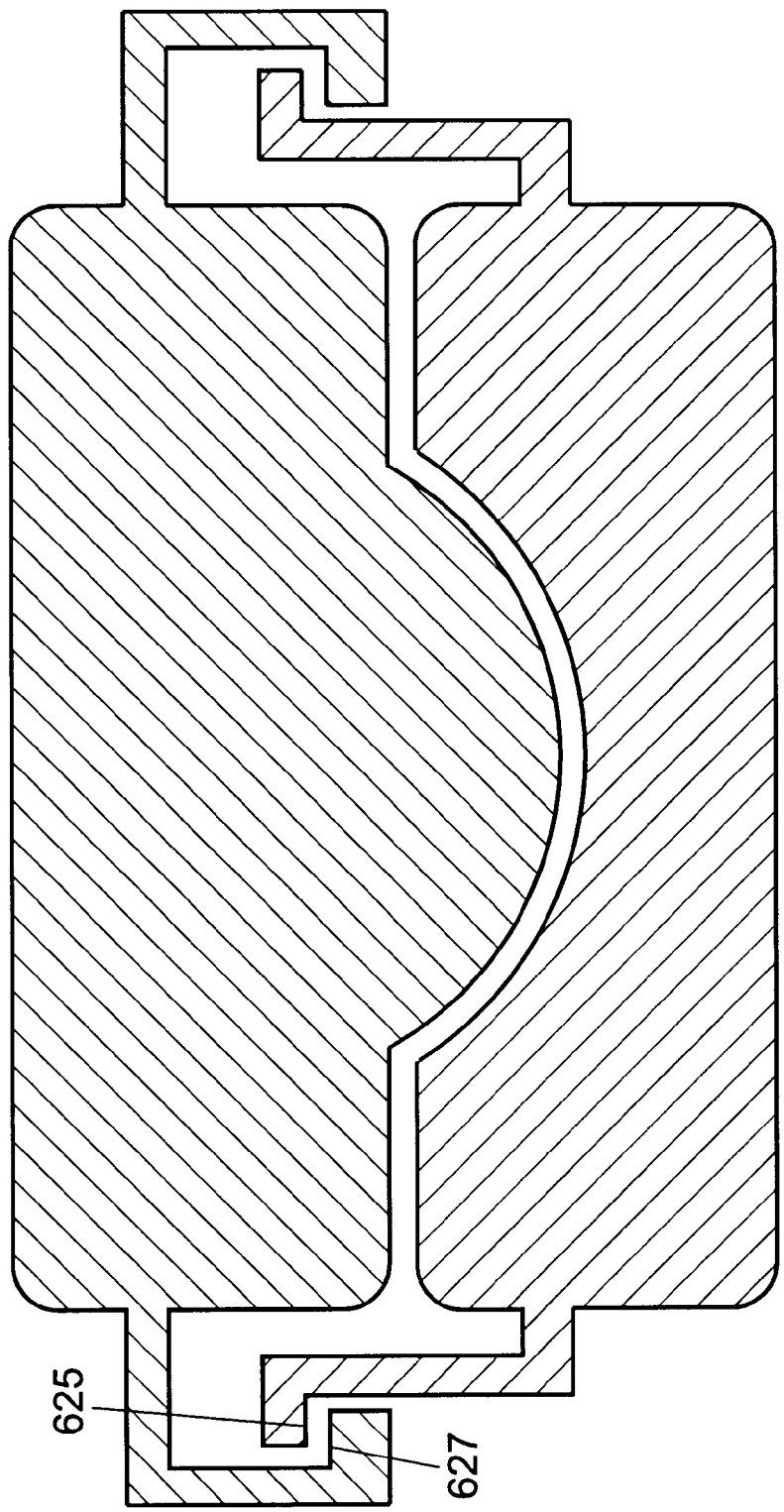

Now referring to FIG. 13, there is provided another embodiment of the present invention in which the projections of the locking means extend from the sidewalls of each and their respective locking surfaces 625,627 form a locking interface located outside the periphery of the prosthetic vertebral endplates and between the prosthetic vertebral endplates.

Figure 14:
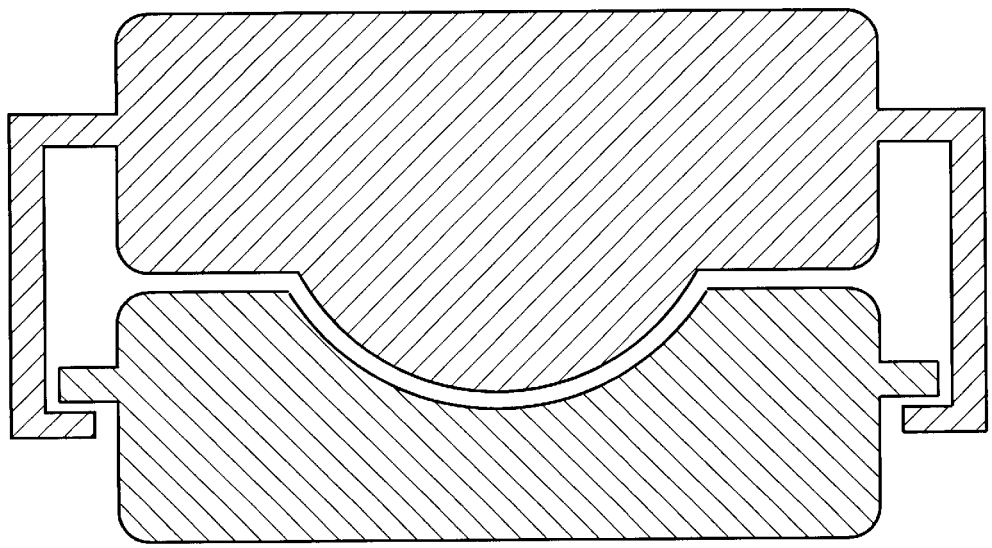

Now referring to FIG. 14, there is provided another embodiment of the present invention which is similar to the device of FIG. 13, except that the locking interface is located towards the lower prosthetic vertebral endplate.

Figure 15:
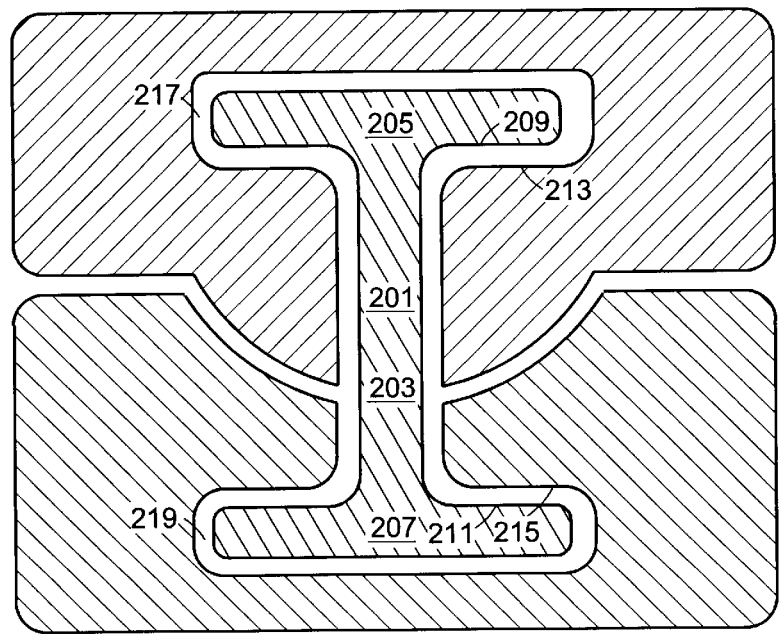

Now referring to FIG. 15, there is provided another embodiment of the present invention further comprising a connector 201 having a shank 203 and first and second end portions 205, 207 forming locking surfaces 209, 211 that are adapted to form a locking interface with the respective locking surfaces 213, 215 located within the respective recesses 217,219 of the two prosthetic vertebral endplates.

Figure 16:
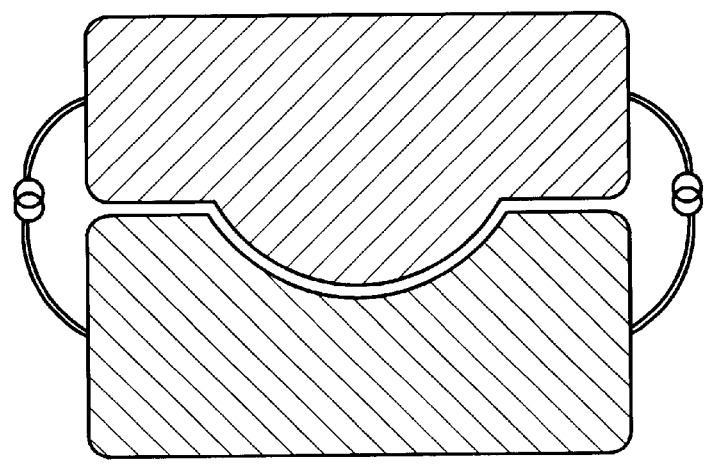

FIG. 16 is substantially similar to FIG. 13, except that the locking means is provided by a pair of interconnected rings.

Figure 17:
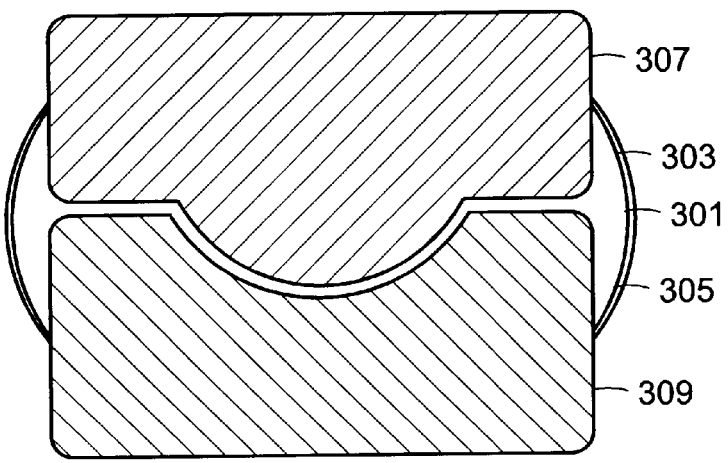

Now referring to FIG. 17, there is provided another embodiment of the present invention further comprising a ligament 301 having first and second end portions 303,305 respectively connected to first and second sidewalls 307, 309 to form the locking means.

Figure 18:
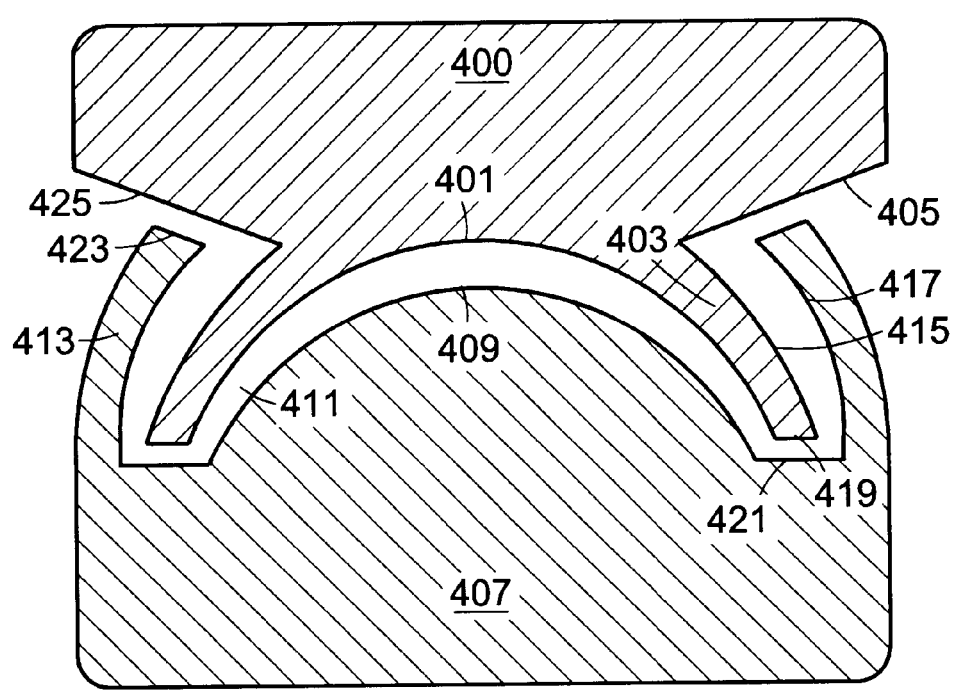

In FIG. 18, upper prosthetic vertebral endplate 400 comprises upper articulation surface 401, radially peripheral projection 403, and outer recess 405, while lower prosthetic vertebral endplate 407 comprises lower articulation surface 409, radially peripheral recess 411, and outer projection 413.

The overlapping arcs of the projections allow outer surface 415 of radially peripheral projection 403 to form a locking interface with the inner surface 417 of outer projection 413 and thereby limit normal disengagement. The gaps between a) the end surface 419 of projection 403 and the deep surface 421 of recess 411, and b) the end surface 423 of projection 413 and the deep surface 425 of recess 405 determine the range of motion of the device.

Figure 19:
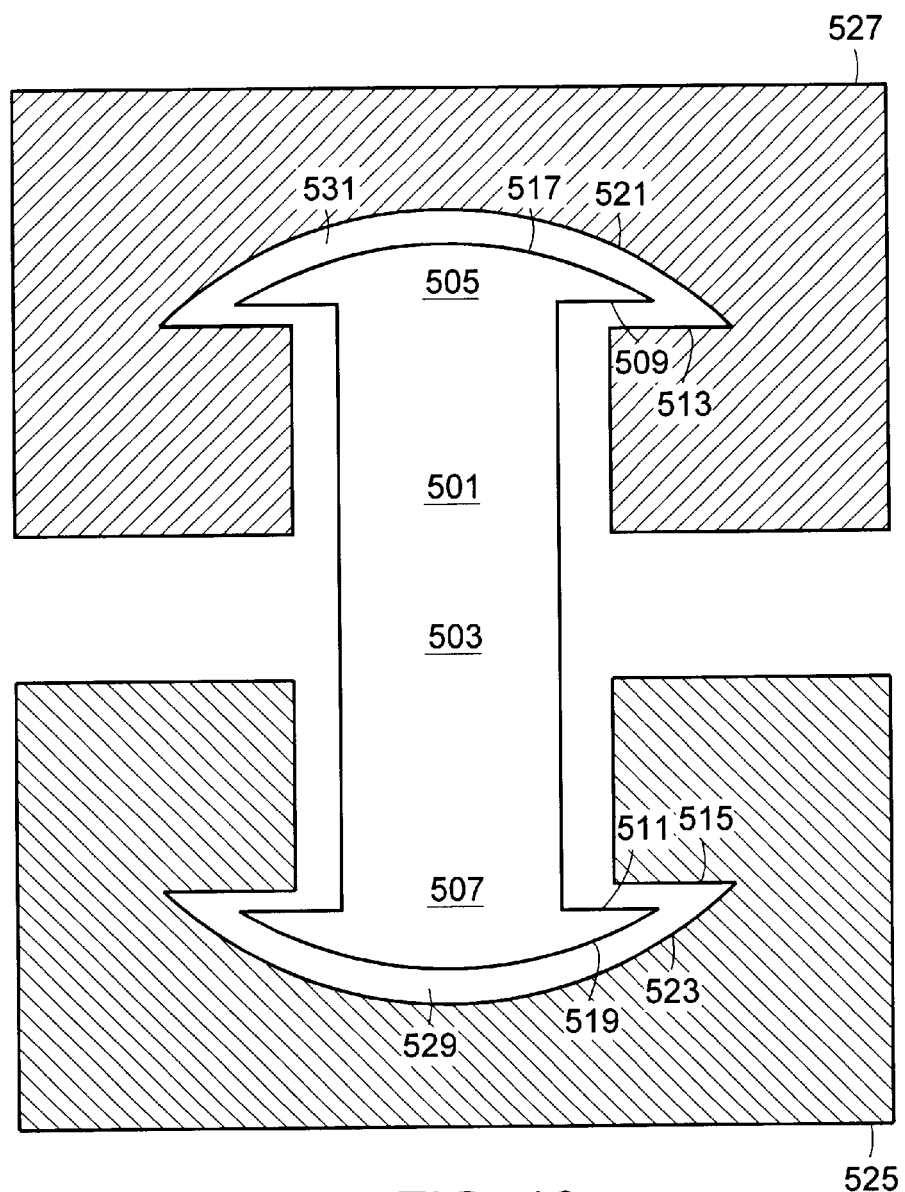

Now referring to FIG. 19, there is provided another embodiment of the present invention further comprising a connector 501 having a shank 503 and first and second end portions 505, 507 comprising both locking surfaces 509,511 that are adapted to form a locking interface with the respective locking surfaces 513, 515 located within the respective recesses of the two prosthetic vertebral endplates 525,527, and articulating surfaces 517,519 that are adapted to form a locking interface with the respective articulating surfaces 521,523 located within the respective recesses 529,531 of the two prosthetic vertebral endplates.

In some embodiments, the locking means is provided by a first component having a first locking surface which is attached to (or is integral with) a first prosthetic vertebral endplate, and a second component having a second locking surface attached to (or is integral with) a second prosthetic vertebral endplate. Generally, the prosthetic vertebral endplates are adapted so that the two locking surfaces contact each other when the outer surfaces of the two prosthetic vertebral endplates move apart, thereby limiting the normal disengagement of the prosthetic vertebral endplates. Examples of locking means provided by a combination of components include a projection-and-recess combination (as in FIGS. 1 and 6), and a pair of projections combination (as in FIGS. 13 and 16), and their structural equivalents.

In other embodiments, the locking means comprises a ligament attached to each prosthetic vertebral endplate whose middle portion experiences tension when the two prosthetic vertebral endplates move apart. The tension so produced limits the normal disengagement of the prosthetic vertebral endplates. Structural equivalents of such integral locking means, including a cable and a spring, a ligament (as in FIG. 17) are also contemplated.

In some embodiments, an element of the locking means may extend from an articulation surface. For example, in FIG. 1, the projection 29 extends from articulation surface 17. In others, an element of the locking means may extend from an inner surface of a prosthetic vertebral endplate but is located outside the articulation surface. For example, in FIG. 11, a projection 601 extends from the peripheral portion 603 of the inner surface and is located between the articulation surface 606 and side wall 608. In others, the elements of the locking means may extend from side walls of the component. For example, in FIG. 12 the projection 611 extends from side wall 613.

In some embodiments, the locking means comprises a pair of opposed locking surfaces adapted to form a locking interface. In some embodiments, the locking interface is disposed substantially parallel to the articulation interface.

In many embodiments, as in FIG. 1, the locking interface is formed by a first locking surface on a first prosthetic vertebral endplate oriented to face the opposite direction of the articulation surface of the first prosthetic vertebral endplate, and a second locking surface on a second prosthetic vertebral endplate oriented to face the opposite direction of the articulation surface of the second prosthetic vertebral endplate. In some embodiments, as in FIG. 19, the device comprises a third component, and the locking interface is formed by a first locking surface on the third component oriented to face the opposite direction of the articulation surface of the first prosthetic vertebral endplate, and a second locking surface on the third component oriented to face the opposite direction of the articulation surface of the second prosthetic vertebral endplate. In some embodiments, as in FIG. 15, the device comprises a third component, and the locking interface is formed by a first locking surface on the third component oriented to face the same direction of the articulation surface of the first prosthetic vertebral endplate, and a second locking surface on the third component oriented to face the same_direction of the articulation surface of the second prosthetic vertebral endplate.

In some preferred embodiments, the locking means comprises a projection extending from a first prosthetic vertebral endplate and a recess extending into a body portion of a second prosthetic vertebral endplate, wherein the projection fits inside the recess. More preferably, the projection extends from the inner surface of the first prosthetic vertebral endplate and the recess extends from the inner surface of the second prosthetic vertebral endplate. In some embodiments, each of the projection and recess have a mushroom shape comprising a narrow first portion and an enlarged end portion. In such embodiments, once the enlarged end portion of the projection is advanced into the enlarged deep portion of the recess, the enlarged end portion of the projection can not be easily pulled out of the recess. Typically, this requires the projection to have an enlarged end portion to possess a diameter that is greater than the diameter of the narrow portion of the recess. Some examples of some mushroom-type locking means will now be disclosed:

Now referring to FIGS. 2 and 3, in one embodiment, the locking means may comprise a mushroom-shaped projection having a enlarged end portion having a rectangular end surface and a mushroom shaped recess having a rectangular shallow portion which is slightly larger than the rectangular end surface of the projection. The projection is advanced through the rectangular portion of the recess by carefully aligning the two rectangular portions. Once the projection has advanced through the shallow portion of the recess, one of the prosthetic vertebral endplates is rotated 90 degrees to lock the enlarged end portion of the projection within the enlarged end portion of the recess.

In other embodiments, the locking means may comprise a mushroom-shaped projection having an enlarged end portion having a D-shaped end surface and a mushroom shaped recess having a corresponding D-shaped shallow portion which is slightly larger than the D-shaped end surface of the projection. This embodiment is similar to the rectangular-shaped means described above, except that the D shapes are aligned only upon 180 degree rotation of the prosthetic vertebral endplates. Accordingly, this embodiment is less likely to become disengaged.

Figure 20:
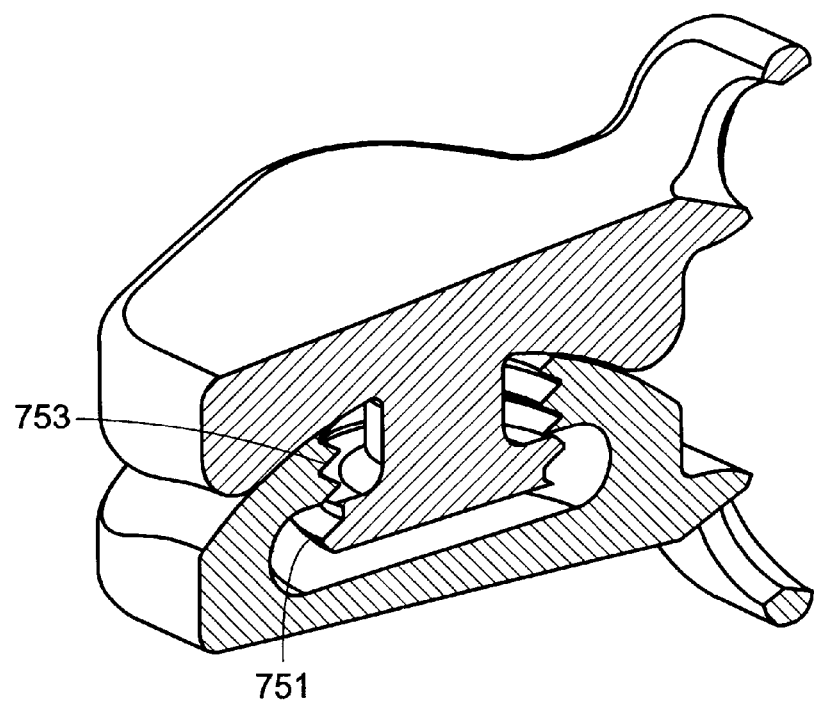
FIG. 20 discloses a cross-sectional view of an embodiment of the present invention having a threaded locking feature.

Now referring to FIG. 20, in one embodiment, the locking means comprises a mushroom-shaped projection having an enlarged threaded end portion 751 and a mushroom shaped recess having a threaded shallow portion 753 which mates with the projection thread. The projection is advanced through the rectangular portion of the recess by screwing the projection head through the shallow portion of the recess. Once the enlarged portion of the head has advanced through the shallow portion of the recess, it can not randomly escape the recess.

In one embodiment, the locking means comprises a mushroom-shaped projection having an anchor-type end portion and a mushroom shaped recess having a shallow portion whose diameter is less than that of the anchor. The projection is advanced through the rectangular portion of the recess by squeezing the anchor through the shallow portion of the recess. Once the enlarged portion of the head has advanced through the shallow portion of the recess, it can not randomly escape the recess.

In one embodiment, the locking means comprises a mushroom-shaped projection having a flexible tab end portion and a mushroom shaped recess having a shallow portion whose diameter is less than that of the tab. The projection is advanced through the rectangular portion of the recess by squeezing the tab through the shallow portion of the recess. Once the enlarged portion of the tab has advanced through the shallow portion of the recess, it can not randomly escape the recess.

In one embodiment, the locking means comprises a projection comprising a memory metal and a mushroom shaped recess. The projection is designed so that its end portion is straight at a first lower temperature and its end is curved at a second higher temperature. The projection is provided at the lower temperature so that the straightened end portion of the projection is easily advanced through the shallow portion of the recess. Once the end portion of the projection has advanced through the shallow portion of the recess, body heat raises the temperature so that the end portion curves so that it can not randomly escape the recess.

In some embodiments, the projection is characterized by a mushroom-type geometry, comprising a narrow shank portion and a enlarged end portion. Preferably, the length of the shank portion is between 0.5 and 5 (preferably, between 1 and 4) times the length of the enlarged end portion. Preferably, the diameter of the shank portion is between 0.25 and 1 times larger than the larger dimension of the enlarged end portion. In some embodiments, the enlarged end portion forms an inner surface 19 extending substantially parallel to the articulation surface. This inner surface may form a portion of the locking interface. In some embodiments, the enlarged end portion has an outer surface shaped to form a portion of an articulating surface 131. In some embodiments, this articulating outer surface describes an arc of between about 1 and 30 degrees, preferably between 5 and 15 degrees.

In some embodiments, the recess is also characterized by a mushroom-type geometry, comprising a narrow shallow portion and a enlarged deep portion. Preferably, the length of the narrow shallow portion is between 1 and 2 times the length of the enlarged deep portion. Preferably, the diameter of the enlarged deep portion is between 1.1 and 3 times larger than the diameter of the narrow shallow portion. In some embodiments, the enlarged deep portion forms an inner locking surface extending from the narrow shallow portion in a substantially orthogonal direction. This inner locking surface may form a portion of the locking interface. In some embodiments, the enlarged deep portion of the recess defines an outer articulating surface shaped to form a portion of an articulating interface. In some embodiments, this outer articulating surface describes an arc of between about 5 and 15 degrees.

In some embodiments, the projection and recess each have an axial cross-section wherein the cross section of the recess is substantially congruent to the cross section of the projection. Preferably, the ratio of the diameter of the enlarged end portion (or "head") of the projection to the diameter of the deep portion of the recess is between 0.25 to 0.75. Preferably, the ratio of the diameter of the shank portion of the projection to the diameter of the shallow portion of the recess is between 0.25 and 0.75.

In some embodiments having a projection and a recess, the projection has a length and the recess has a depth, and the depth of the recess is greater than the length of the projection. Preferably, the depth of the recess is between 10% and 50% greater than the length of the projection.

The present invention may also comprise a means for restraining the pivotal motion of the device to limit the pivotal motion of the articulating interface to a desirable arc. Accordingly, in accordance with the present invention, there is provided a motion disc comprising:
 a) an upper prosthetic vertebral endplate having a first surface and an second surface,
 b) a lower prosthetic vertebral endplate having a first surface and an second surface,
 c) means for restraining pivotal movement of the upper prosthetic vertebral endplate to the lower prosthetic vertebral endplate,
wherein at least a portion of the second surface of the upper prosthetic vertebral endplate and at least a portion of the first surface of the lower prosthetic vertebral endplate form a conforming articulating interface, and
 wherein the means for restraining pivotal movement is encompassed by the articulating surface.

In some embodiments, the means may act to limit the pivotal anterior-posterior motion of the articulating interface to between 1 and 30 degrees, and preferably about 13 degrees. In some embodiments, the relative shapes of the projection and recess act to limit the pivotal lateral motion of the articulating interface to between 1 and 30 degrees, and preferably about 6 degrees.

In other embodiments, the means for restraining pivotal motion may comprise a shock-absorbing material disposed within the deep portion of the recess. Preferably, this material is formed into a donut shape and rings the deep portion of the recess so as to contact the enlarged head of the projection during extreme cases of pivotal motion, thereby gently limiting the extent of pivotal motion. In other embodiments, the shock-absorbing material may be placed in the shallow portion of the recess and similarly limit the motion of the shank portion of the projection.

The articulating interface of the present invention can be either conforming or nonconforming. Preferably, it is a conforming interface. If a non-conforming interface is selected, the surfaces thereof are preferably provided with an outer layer of a wear-resistant material, such as a TiN coating or diamond film coating. The articulating surfaces are preferably highly polished to a surface roughness Ra of no more than 10 nm to limit the wear debris generation. This surface roughness can be produced using conventional polishing methods.

In some embodiments, the articulation interface comprises a curved bearing interface. The curved bearing interface can be selected from the group consisting of hemispherical, cylindrical, ellipsoidal and oblong. The articulation surface can provide at least one of pivotal motion, axial rotational motion, and translation motion, and combinations thereof. In one preferred embodiment, the articulation surface provides both pivotal motion and axial rotational motion.

In some embodiments of the present invention (such as FIG. 2), the locking means may be located within a body portion of one of the prosthetic vertebral endplates and the articulation surface may be located upon the inner surfaces of the prosthetic vertebral endplates. Preferably, the articulation surface of this embodiment extends to include the periphery of the inner surfaces. This arrangement provides a greater amount of surface area for articulation, thereby reducing the pressure upon the articulation interface and therefore the potential for wear. In some embodiments, at least 80% (and preferably, at least 90%) of the surface area of an inner surface of a prosthetic vertebral endplate is an articulation surface.

Figure 21:
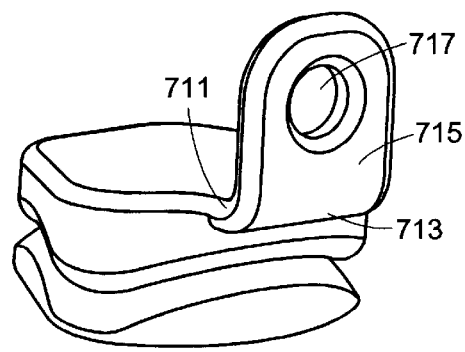
FIG. 21 discloses a perspective view of an embodiment having a tab extending from an upper prosthetic vertebral endplate.
Figure 22:
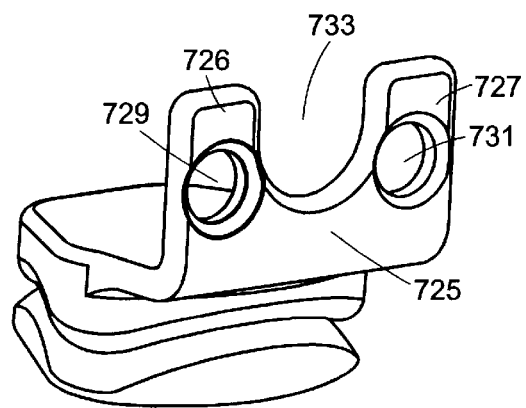
FIG. 22 discloses a perspective view of an embodiment having a dual-holed tab extending from an upper prosthetic vertebral endplate.

Short term fixation can be employed by any conventional means, including providing at least one prosthetic vertebral endplate with an angled hole for the insertion of a bone screw therethrough. In some embodiments, the anterior side of at least one prosthetic vertebral endplate is provided with an extension (or a "tab") having a hole therethrough for the reception of a screw. Now referring to FIG. 21, a proximal portion 711 of a tab 713 extends horizontally from the sidewall of an upper prosthetic vertebral endplate and then bends about 90 degrees to form a vertically-disposed distal portion 715 having a hole 717 therethrough for reception of a fastener such as a screw. Now referring to FIG. 22, the vertically-disposed distal portion 725 comprises two tongues 726, 727 having holes 729, 731 therethrough for reception of fasteners. Formed between the pair of tongues is a nest 733.

Figure 23:
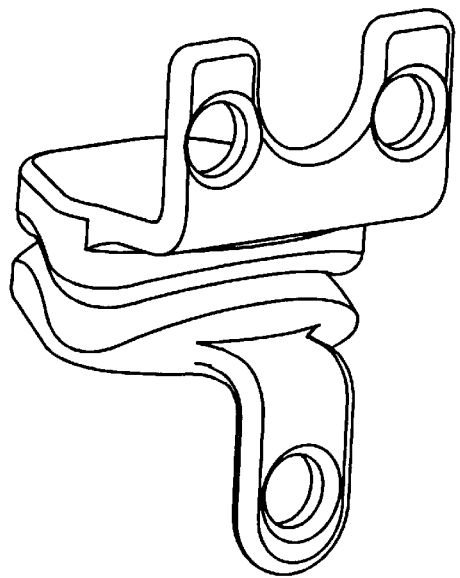
FIG. 23 discloses a perspective view of an embodiment having a dual-holed tab extending from an upper prosthetic vertebral endplate, and a single holed tab extending from a lower prosthetic vertebral endplate.

FIG. 23 discloses a perspective view of an embodiment having an upper prosthetic vertebral endplate having a pair of tongues forming a nest, and a single-holed tab extending from a lower prosthetic vertebral endplate. The periphery of the lower tab matches the shape of the nest formed in the upper tab. Accordingly, when more than one of these devices are used in adjacent vertebrae, the downward-extending single-holed tab of the upper device can fit into the upward-facing nest of the lower device, thereby allowing the devices to efficiently overlap.

Long term fixation may be accomplished by providing a porous coating suitable for bone ingrowth upon the outer surfaces of the first and second prosthetic vertebral endplates. In addition, the outer surfaces of the first and second prosthetic vertebral endplates can be flat (as in FIG. 1), or, each can have dome contours (as in FIG. 5) for better long term fixation. Cutting tools which shape the adjacent vertebral endprosthetic vertebral endplates to match the contours of the device's outer surfaces can be used. In some embodiments, the outer surfaces of the first and second prosthetic vertebral endplates have teeth extending therefrom to aid in fixation. In some embodiments, these teeth form pyramid shapes. The footprint of the endprosthetic vertebral endplates can have any conventional shape, including but not limited to substantially trapezoidal, substantially circular, substantially oval, substantially kidney-shaped, and substantially square.

If a tension-producing locking means is used, it is preferably directly attached to a side wall of each prosthetic vertebral endplate. However, in some embodiments, it may be attached to a surface within a recess extending either from a side wall of a prosthetic vertebral endplate, or from an inner surface of each prosthetic vertebral endplate.

The prosthetic vertebral endplates of the present invention may be manufactured by conventional metal forming technology, including pouring molten metal into molds. In some preferred embodiments, first and second prosthetic vertebral endplates are made from CoCr alloy. Articulation surfaces may be polished to a surface roughness Ra of no more than about 10 nm by conventional means. Projections used to form locking surfaces can be made integral with a first prosthetic vertebral endplate, or made as a separate component and then attached to the first prosthetic vertebral endplate. Preferably, each prosthetic vertebral endplate is sterile.

In use, a problematic disc is removed by the surgeon and the disc space created is cleaned of any remaining cartilaginous material. Next, the endplates of the opposing vertebrae are shaped to match the shapes of the outer surfaces of each prosthetic vertebral endplate.

Preferably, the disc of the present invention is used in a sterile condition. To assemble and lock the disc of FIG. 1, the shapes of enlarged end portion of projection and the shallow portion of the recess are first aligned, the first prosthetic vertebral endplate is then pushed down until the enlarged end portion of projection passes through the shallow portion and into deep portion 27. Next, the prosthetic vertebral endplates are rotated about 90 degrees in relation to each other, and the enlarged head of the projection will correspondingly turn and become locked in the deeper portion of the recess, thereby limiting the extent of separation of the articulating surfaces, but allowing pivotal motion axial rotation and, if desired, translation.

Next, the surgeon places the locked device of the present invention into the disc space so that the outer surface of a first prosthetic vertebral endplate of the device snugly contacts the upper vertebral endplate, and the outer surface of a second prosthetic vertebral endplate of the device snugly contacts the lower vertebral endplate. Lastly, the surgeon provides short term fixation.

We claim:

1. A motion disc comprising:
   a) a first prosthetic vertebral endplate having
      i) an outer surface adapted to mate with a first vertebral body,
      ii) an inner surface comprising a first articulation surface,
      iii) a first body portion between the inner and outer surfaces of the first prosthetic vertebral endplate
   wherein the inner surface of the first prosthetic vertebral endplate has a recess extending therefrom into the first body portion and forming a first locking surface and a first articulation surface, and
   b) a second prosthetic vertebral endplate having
      i) an outer surface adapted to mate with a second vertebral body,
      ii) an inner surface comprising a second articulation surface,
      iii) a second body portion between the inner and outer surfaces of the second prosthetic vertebral endplate,
   wherein the inner surface of the second prosthetic vertebral endplate has a recess extending therefrom into the second body portion and forming a second locking surface and a second articulation surface, and
   c) a connector comprising a shank and first and second end portions,
   wherein the first end portion of the connector comprises a first locking surface and a first articulation surface, and
   wherein the second end portion of the connector comprises a second locking surface and a second articulation surface,
   wherein the first and second articulation surfaces are adapted to form an articulating interface, and
   wherein the first and second locking surfaces are adapted to form a locking interface.

2. The disc of claim 1 wherein the inner surface of the first prosthetic vertebral endplate has a projection extending therefrom, and the locking surface of the first prosthetic vertebral endplate is formed on the projection.

3. The disc of claim 2 wherein the projection extends from the first articulation surface.

4. The disc of claim 2 wherein the inner surface of the first prosthetic vertebral endplate further comprises a non-articulating surface, and the projection extends from the non-articulating surface.

5. The disc of claim 4 wherein the non-articulating surface is disposed upon the inner surface peripherally to the articulating surface.

6. The disc of claim 2 wherein the projection comprises a shank having a diameter and an enlarged end portion having a diameter, and the diameter of the enlarged end portion is greater than the diameter of the shank.

7. The disc of claim 6 wherein the articulation surface of the first prosthetic vertebral endplate is formed on the enlarged end portion of the projection.

8. The disc of claim 7 wherein the articulation surface forms an arc of between 5 degrees and 15 degrees.

9. The disc of claim 1 further comprising a sidewall disposed between the inner and outer surfaces of the first prosthetic vertebral endplate, and wherein the sidewall of the first prosthetic vertebral endplate has a projection extending therefrom, and the locking surface of the first prosthetic vertebral endplate is formed on the projection.

10. The disc of claim 2 wherein the first prosthetic vertebral endplate is an upper prosthetic vertebral endplate, and the second prosthetic vertebral endplate is a lower prosthetic vertebral endplate.

11. The disc of claim 10 wherein the first articulation surface is convex.

12. The disc of claim 10 wherein the first articulation surface is concave.

13. The disc of claim 2 wherein the first prosthetic vertebral endplate is a lower prosthetic vertebral endplate, and the second prosthetic vertebral endplate is an upper prosthetic vertebral endplate.

14. The disc of claim 13 wherein the first articulation surface is convex.

15. The disc of claim 13 wherein the first articulation surface is concave.

16. The disc of claim 1 further comprising a body portion between the inner and outer surfaces of the first prosthetic vertebral endplate, wherein the inner surface of the second prosthetic vertebral endplate has a recess extending therefrom into the body portion, and the locking surface of the second prosthetic vertebral endplate is formed in the recess.

17. The disc of claim 16 wherein the recess extends from the second articulation surface.

18. The disc of claim 16 wherein the inner surface of the second prosthetic vertebral endplate further comprises a non-articulating surface, and the recess extends from the non-articulating surface.

19. The disc of claim 18 wherein the non-articulating surface is disposed upon the inner surface peripherally to the articulating surface.

20. The disc of claim 16 wherein the recess comprises a shallow portion having a diameter and a deep portion having a diameter, and the diameter of the deep portion is greater than the diameter of the shallow portion.

21. The disc of claim 20 wherein the articulation surface of the second prosthetic vertebral endplate is formed on the deep portion of the recess.

22. The disc of claim 21 wherein the articulation surface of the second prosthetic vertebral endplate forms an arc of between 5 degrees and 15 degrees.

23. The disc of claim 16 further comprising a sidewall disposed between the inner and outer surfaces of the second prosthetic vertebral endplate, and wherein the sidewall of the second prosthetic vertebral endplate has a recess extending therefrom into the body portion, and the locking surface of the second prosthetic vertebral endplate is formed in the recess.

24. The disc of claim 1 further comprising a body portion between the inner and outer surfaces of the second prosthetic vertebral endplate,
   wherein the inner surface of the second prosthetic vertebral endplate has a recess extending therefrom into the body portion, and the locking surface of the second prosthetic vertebral endplate is formed in the recess, and
   wherein the inner surface of the first prosthetic vertebral endplate has a projection extending therefrom, and the locking surface of the first prosthetic vertebral endplate is formed on the projection.

25. The disc of claim 24 wherein the projection comprises a shank having a diameter and an enlarged end portion having a diameter, and the diameter of the enlarged end portion is greater than the diameter of the shank, and the recess comprises a shallow portion having a diameter and a deep portion having a diameter, and the diameter of the deep portion is greater than the diameter of the shallow portion.

26. The disc of claim 25 wherein the diameter of the enlarged end portion of the projection is between 25% and 75% of the diameter of the deep portion of the recess.

27. The disc of claim 25 wherein the diameter of the shank of the projection is between 25% and 75% of the diameter of the shallow portion of the recess.

28. The disc of claim 25 wherein the diameter of the deep portion of the recess is between 1.1 and 3 times greater than the diameter of the shallow portion of the recess.

29. The disc of claim 25 wherein the diameter of the shank of the projection is 25% to 99% of the diameter of the enlarged end portion of the projection.

30. The disc of claim 24 wherein the projection is integrally connected to the first prosthetic vertebral endplate.

31. The disc of claim 24 wherein the projection extends from the first articulation surface, and wherein the inner surface of the first prosthetic vertebral endplate has a surface area, and the first articulation surface comprises at least 80% of the surface area of a footprint of the first prosthetic vertebral endplate.

32. The disc of claim 24 wherein the enlarged end portion of the projection forms a rectangular shape.

33. The disc of claim 24 wherein the enlarged end portion of the projection comprises a threaded portion.

34. The disc of claim 24 wherein the enlarged end portion of the projection forms an anchor.

35. The disc of claim 24 wherein the enlarged end portion of the projection comprises a flexible tab.

36. The disc of claim 24 wherein the enlarged end portion of the projection comprises a memory metal.

37. The disc of claim 1 further comprising a first sidewall disposed between the inner and outer surfaces of the first prosthetic vertebral endplate, and wherein the first sidewall of the first prosthetic vertebral endplate has a first projection extending therefrom, and the locking surface of the first prosthetic vertebral endplate is formed on the first projection, and a second sidewall disposed between the inner and outer surfaces of the second prosthetic vertebral endplate, and wherein the second sidewall of the second prosthetic vertebral endplate has a projection extending therefrom, and the locking surface of the second prosthetic vertebral endplate is formed on the second projection.

38. The disc of claim 1 wherein the locking surface of the first prosthetic vertebral endplate faces a first direction, and the articulation surface of the first prosthetic vertebral endplate faces in a second direction, and the first direction is substantially opposite the second direction.

39. The disc of claim 1 wherein the first prosthetic vertebral endplate further comprises a tab extending therefrom and forming a vertically-disposed distal portion forming a pair of tongues, each tongue having a hole therethrough for reception of a fastener, wherein the tongues form a nest therebetween.

40. The disc of claim 1 wherein the outer surface of the first prosthetic vertebral endplate comprises at least one projection extending therefrom and having a pyramid shape.

* * * * *